(12) United States Patent
McNair

(10) Patent No.: US 11,395,635 B1
(45) Date of Patent: *Jul. 26, 2022

(54) FORECASTING ACUTE INFLAMMATORY CONDITION AND DECISION SUPPORT TOOL

(71) Applicant: CERNER INNOVATION, INC., Kansas City, KS (US)

(72) Inventor: Douglas S. McNair, Leawood, KS (US)

(73) Assignee: CERNER INNOVATION, INC., North Kansas City, MO (US)

( * ) Notice: Subject to any disclaimer, the term of this patent is extended or adjusted under 35 U.S.C. 154(b) by 615 days.

This patent is subject to a terminal disclaimer.

(21) Appl. No.: 16/237,201

(22) Filed: Dec. 31, 2018

Related U.S. Application Data

(60) Provisional application No. 62/612,421, filed on Dec. 30, 2017.

(51) Int. Cl.
  *A61B 5/00*  (2006.01)
  *A61B 5/0205*  (2006.01)
  (Continued)

(52) U.S. Cl.
  CPC .......... *A61B 5/7275* (2013.01); *A61B 5/0205* (2013.01); *A61B 5/412* (2013.01);
  (Continued)

(58) Field of Classification Search
  None
  See application file for complete search history.

(56) References Cited

U.S. PATENT DOCUMENTS 10,390,765 B1 * 8/2019 McNair ............... A61B 5/0015
2008/0311554 A1 * 12/2008 Slotman ............... G01N 33/88
435/4

(Continued)

OTHER PUBLICATIONS

Catastrophe Theory, 1996, The Exploratorium, <"https://www.exploratorium.edu/complexity/CompLexicon/catastrophe.html">. (Year: 1996).*

*Primary Examiner* — Alex M Valvis
*Assistant Examiner* — Aurelie H Tu
(74) *Attorney, Agent, or Firm* — Shook, Hardy & Bacon L.L.P.

(57) ABSTRACT

A catastrophe-theoretic approach is provided for predicting an occurrence of an acute inflammatory condition or event (e.g., SIRS or sepsis) for a human patient based on a time series of monitored vital signs values measured from a patient, and in some instances, for providing advanced notice to clinicians or caregivers when such an acute inflammatory event is forecasted or modifying treatment for the patient, according to the predicted likelihood. In particular, an acute inflammatory condition management system is provided for determining a likelihood of near-term future significant acute inflammation in human patients. Embodiments of the disclosure described herein may provide a forecasted risk for future significant acute inflammation within a time horizon comprising a future time interval. In one embodiment, the future time interval is from 30 min to approximately 8 hours into the future, and may be dependent on the frequency of vital signs measurements.

20 Claims, 9 Drawing Sheets

(51) Int. Cl.
*G16H 50/50* (2018.01)
*A61B 5/08* (2006.01)
*A61B 5/024* (2006.01)
*A61B 5/021* (2006.01)

(52) U.S. Cl.
CPC .............. *G16H 50/50* (2018.01); *A61B 5/021* (2013.01); *A61B 5/024* (2013.01); *A61B 5/0816* (2013.01)

(56) References Cited

U.S. PATENT DOCUMENTS

| | | | | |
|---|---|---|---|---|
| 2009/0292180 | A1* | 11/2009 | Mirow | G16H 10/20 600/301 |
| 2011/0190650 | A1* | 8/2011 | McNair | A61B 5/00 600/518 |
| 2014/0135859 | A1* | 5/2014 | Bardy | A61B 5/349 607/3 |
| 2019/0167209 | A1* | 6/2019 | Annoni | A61B 5/0816 |

* cited by examiner

```
##########################################################

#   Cusp Catastrophe Decision Support Tool For Pre-Sepsis Cases

#################################################### library(cusp)

load data
mon1 <- read.csv(file="c:/0_cerdsm/IP/presepsis/dsm_presepsis.csv", header=TRUE,
        colClasses=c(rep("character",3),rep("numeric",5)))
# enc, dt, key, sbp, sbp2, hr, rpp, rr
mon1 <- mon1[,-c(2,3,5)]

case <- read.csv(file="c:/0_cerdsm/IP/presepsis/cases.csv", header=TRUE, colClasses="character")
len1 <- length(case)
cs <- as.integer(rownames(unique(case)))
len2 <- length(cs)
cs <- c(cs, len2)

# calculate models and determine presence/absence of pre-sepsis signal in smoothed AIC
exceedance # time series
for (k in 1:len2) {
  len3 <- cs[k+1] - cs[k]
  mon2 <- mon1[seq(cs[k]:(cs[k+1]-1)),]
  # inits
  N <- length(mon2[,1]) - 40
  AIC.ts <- rep(0, N)
  perf <- rep(" ", N)
  tol <- 0.2
  thresh <- 0.6
  alarm.presepsis <- rep(0, N)
  ewma <- 0
  # calculate time series of AIC differences between cusp model and linear model
  for (i in 1:N){
    seg <- mon2[i:(39+i),-1]
    # add small amount of noise in case some variables have stretches of constant values
    seg[,1] <- seg[,1] + rnorm(40,0,0.1)
    seg[,2] <- seg[,2] + rnorm(40,0,0.1)
    seg[,3] <- seg[,3] + rnorm(40,0,0.1)
    seg[,4] <- seg[,4] + rnorm(40,0,0.1)
    # center and standardize each time series to SD=1
    seg[,1] <- scale(seg[,1], center=TRUE)
    seg[,2] <- scale(seg[,2], center=TRUE)
    seg[,3] <- scale(seg[,3], center=TRUE)
    seg[,4] <- scale(seg[,4], center=TRUE)
    # calculate cusp and linear models
    set.seed(1239)
    fit <- cusp(y ~ rr, alpha ~ rpp, beta ~ hr, data=seg)
    # determine log Hessian and convergence properties
    perf[i] <- paste0('N: ', i,' OK: ', fit$OK,' conv:', fit$converged)
    # compare linear vs. cusp models AIC values
    fit.res <- summary(fit)
    AIC.ts[i] <- 1*(fit.res$r2cusp.aicc[1] > fit.res$r2lin.aicc + tol)
    # calculate EWMA of log signal
    if (i > 2) ewma <- 0.6*log(AIC.ts[i] + 1) + 0.3*log(AIC.ts[i-1] + 1) + 0.1*log(AIC.ts[i-2] + 1)
    if (ewma > thresh) alarm.presepsis[i] <- 1
  }
  # summary(fit)
  # plot(alarm.presepsis[10:N], ty="l", col="red", lwd=2)
}
```

FIG. 5.

```
###########################################################

#  generate receiver operating characteristic (ROC) curves

##################################################### library(pROC)

ds4 <- read.csv(file="c:/0_cerdsm/IP/presepsis/roc.csv")
roc1 <- roc(ds4[,1] ~ ds4[,2], percent=TRUE,
# arguments for auc
# partial.auc=c(100, 90), partial.auc.correct=TRUE,
# partial.auc.focus="sens",
# arguments for ci
  ci=TRUE, boot.n=100, ci.alpha=0.9, stratified=FALSE,
# arguments for plot
# auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

# column-major
dsm <- matrix(c(40,4,10,56), ncol=2)
fisher.test(dsm)
# p-value = 4.78e-16
# 95 percent confidence interval:
#   14.82 249.9
# odds ratio
#   52.63099
# sens = 91
# spec = 82
# NPV = 92
# PPV = 80
```

*FIG. 6.*

FORECASTING ACUTE INFLAMMATORY CONDITION AND DECISION SUPPORT TOOL

CROSS-REFERENCE TO RELATED APPLICATIONS

This application claims the benefit of U.S. Provisional Application No. 62/612,421, titled "Forecasting Acute Inflammatory Condition And Decision Support Tool," filed Dec. 30, 2017, which is hereby expressly incorporated by reference in its entirety.

BACKGROUND

Acute inflammatory disorders, including sepsis, are an exceedingly common source of excess morbidity and mortality in acute care. Early detection of the presence of acute inflammatory conditions in patients admitted to hospital often enables more effective therapeutic treatments and results in more favorable clinical outcomes than occur when such conditions are not detected until fully manifested. Unfortunately, the detection of symptoms and physiologic abnormalities is in many instances delayed, and such conditions may be relatively well established before computerized-decision support-aided detection or even clinical suspicion of the condition occurs. Acute systemic inflammatory conditions represent one class of conditions for which early diagnosis is particularly desirable, with sepsis being the most serious, and perhaps the most difficult to clinically diagnose.

Sepsis is the result of the interaction of a pathogenic microorganism and its metabolic products (such as lipopolysaccharide [LPS] or other endotoxin products) with a host's defense system that leads to acute systemic inflammation. Characterizing sepsis in a host, however, is made very complex by the number and heterogeneity of factors that play into the final outcome. For instance, the presence of underlying disease, a patient's genetically determined responses to inflammatory stimuli, the general status of his/her immune system, and the microbial mediators and virulence factors released by infectious organisms, among other factors, all contribute to the disease course. Moreover, the process by which this occurs is often remarkably rapid, leaving the clinician with little time or opportunity to identify the emergence of an acute inflammatory condition. While there have been attempts to provide a technological solution through decision support systems, these systems have significant drawbacks and cannot provide the reliability and accuracy of the systems and processes proposed in the present disclosure.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Improved monitoring and decision support technology is provided for human patients who may be prone to an acute inflammatory condition, such as sepsis. In particular, a mechanism is provided, which may be embodied as a computerized decision support tool, to predict or determine the presence, identity, and/or severity of the acute inflammatory condition, based on a time series of monitored physiological values measured from a patient. Embodiments of the disclosure described herein may provide a forecasted risk for the emergence of an acute inflammatory disorder within a time horizon comprising a future time interval. In one embodiment, which may be used for sepsis, the future time interval is from 30 min to approximately 8 hours into the future, and may be dependent on the frequency of a patient's physiological measurements. In some instances, the mechanism further provides advanced notice to clinicians or caregivers when such a condition is detected or forecasted or modifies (or recommends modifying) treatment for the patient, according to the predicted likelihood.

A catastrophe-theoretic approach is provided, for forecasting emergence of the acute inflammatory disorder or event, which does not require patient measurements to be acquired on a regular or periodic basis. In particular, emerging alterations in the inter-relationships of cardiovascular time series and respiratory time series may be detected in a timely manner in cardiorespiratory patterns that form a "prodrome" that in many instances precedes the onset of systemic inflammatory response syndrome (SIRS) or sepsis. In one aspect, a vital signs time series is determined for a candidate patient. From the time series, a linear model and cusp catastrophe model is calculated, and goodness-of-fit measures are determined. A likelihood of future acute inflammatory disorder emergence is then determined within a future time interval, based on whether threshold for the smoothed cusp model is transgressed or, alternately, based on whether a threshold for the ratio of linear-to-cusp model values is exceeded. Based on the determined likelihood, a set of one or more actions may be initiated. One action comprises generating a notification that may be emitted or otherwise communicated to a provider clinician(s) responsible for the care of the patient. Another action that may be initiated, based on the determined likelihood of elevated risk of evergence, comprises a recommendation for modifying a care plan or treatment procedure associated with the patient. Yet another action that may be initiated, based on the determined likelihood, comprises automatically modifying computer code executed in a healthcare software program for treating the patient, thereby transforming the program at runtime.

Accordingly, one aim of embodiments of this disclosure is to improve upon conventional industry practices and decision support technology. For example, one aim of the embodiments of this disclosure is to reduce or eliminate the need for expensive laboratory tests and specialized machinery. The cost associated with conventional industry practice is due in part on its reliance on exotic variables, which can only be measured using expensive laboratory tests or specialized machinery. The expense and availability of these laboratory tests and machinery has a significant impact on treating a patient. The costs involved with these laboratory tests or machinery often leave diseases undiagnosed and under-treated. In some instances, the expense will cause a caregiver to hesitate in pursuing these laboratory tests and machinery. It is not unusual that these laboratory tests and machinery are only sought when the health of the patient has already dramatically declined. However, by employing the technologies described herein, the expense associated with the conventional industry practice can be eliminated as the embodiments described herein do not require these expensive laboratory tests or machinery. Moreover, the improvements offered by the embodiments described herein have a significant impact on the health of the patient as the instant technology can be employed at a lower expense and on a preventive basis, without any indication of a patient's decline in health. Consequently, embodiments of these technologies provide life-saving implications as the clinical decision support technology described herein can be employed prior to a decline in the patient's health. In addition, the embodiments described herein enable hospitals and medical centers to offer the instant clinical decision support technology without the significant investment in the additional laboratory equipment or machinery.

Another aim is to improve upon the accuracy of conventional industry practices and decision support technology. As described above, the expense involved with the conventional industry practice usually make it cost-prohibitive. However, even if these expensive laboratory tests and machinery are sought, they render less accurate results. For instance, the expensive laboratory tests and machinery typically produce a greater amount of noise, which decreases the rate of accuracy as there are higher rates of false positives and false negatives. As such, the outcome of these conventional technologies fail to be as reliable as embodiments of this disclosure. As described herein, conventional technologies are only capable of achieving a 35% sensitivity rate of certainty while the technology described herein is capable of achieving a 91% sensitivity rate. Accordingly, embodiments offer a significant improvement over the accuracy of achieved through conventional industry practices.

An additional aim is to enable a determination based on a leading indicator as opposed to a lagging indicator. Conventional decision support technology relies on late, lagging indicators. However, by employing the technologies described herein, the decision support technology does not need to rely on the lagging indicators that are typically required by conventional technology.

Other improvements relate to deriving more accurate predictive capabilities (versus conventional computerized-decision support technologies or medical practices) from even moderate-frequency, potentially-aperiodic time series such as that which may be readily obtained with monitoring in acute care environments. In this way, embodiments described herein overcome deficiencies in the prior art as they are robust (a) against temporary sensor artifacts or intermittent gaps or failures to perform periodic measurements, (b) against delays in uploading or synchronizing newly acquired patient physiological values with historical vital signs time series measured in the patient, and (c) against non-stationarity in the time series, such as may arise during periods when the patient's health deviates from predominant patterns, due to health conditions or physiologic phenomena that alter autonomic sympathetic-parasympathetic tone and neuroendocrine regulation, such as when the patient has systemic inflammatory response syndrome (SIRS) or sepsis. Moreover, forecasting one or more event occurrences within a near-term future interval, such as a 4-hour time horizon, provides a valuable benefit. Such a timeframe is long enough that an actionable occurrence is quite likely for many patients, but not so long that the risk of the event is omnipresent such that alert signals become annoying or a cause of "alert fatigue".

BRIEF DESCRIPTION OF THE DRAWINGS

The present invention is described in detail below with reference to the attached drawing figures, wherein:

FIG. 5 illustratively provide an example embodiment of a computer program routine for predicting an occurrence of an acute inflammatory disorder or event for a human patient within a future time interval, in accordance with an embodiment of the disclosure; and FIG. 6 illustratively provides an example embodiment of a computer program routine for generating a receiver operating characteristic (ROC) curve of the forecasting system and method set forth in the invention for an embodiment of the disclosure described in connection with the method of FIG. 2.

DETAILED DESCRIPTION

Figure 1A:
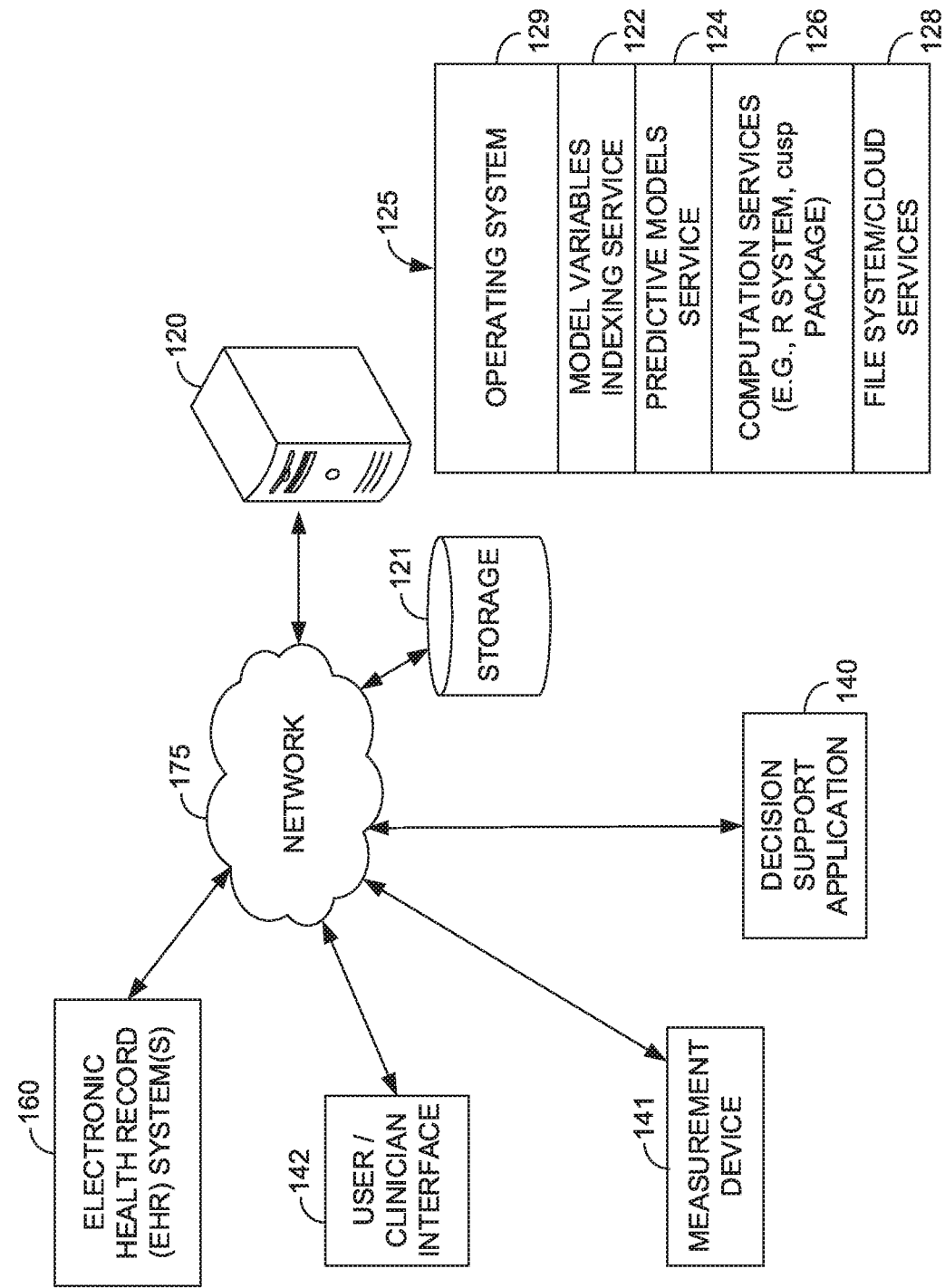
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media, which is described herein. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

At a high level, this disclosure describes, among other things, methods and systems, for predicting an occurrence of an acute inflammatory condition or event based on a time series of monitored vital signs values measured from a patient, and in some instances, for providing advanced notice to clinicians or caregivers when such a condition or event is forecasted or modifying treatment for the patient, according to the predicted likelihood. Embodiments of the disclosure described herein may provide a forecasted risk for future significant elevated risk of an acute inflammatory disorder or events within a time horizon comprising a future time interval. In one embodiment, the future time interval is from 30 min to approximately 8 hours into the future, and may be dependent on the frequency of vital signs measurements.

In some embodiments, a catastrophe-theoretic approach is provided, for forecasting emergence of the acute inflammatory disorder, which does not require patient measurements to be acquired on a regular or periodic basis. In particular, emerging alterations in the inter-relationships of cardiovascular time series and respiratory time series may be detected in a timely manner in cardiorespiratory patterns that form a "prodrome" that in many instances precedes the onset of systemic inflammatory response syndrome (SIRS) or sepsis. In one aspect, a vital signs time series is determined for a candidate patient. In one embodiment, the time series comprises at least 40 measurements, and in one embodiment, the values of the vital-signs variables may be standardized and/or centered. From the time series, a linear model and cusp catastrophe model is calculated, and goodness-of-fit measures may be determined. In one embodiment, the goodness-of-fit measure comprises the Akaike Information Criterion (AIC). Further, in one embodiment, the time series may be smoothed such as by applying using Exponentially-Weighted Moving Average (EWMA). A likelihood of future acute inflammatory condition or event occurrence is then determined within a future time interval, based on whether threshold for the smoothed cusp model is transgressed or, alternately, based on whether a threshold for the ratio of linear-to-cusp model values is exceeded. In one embodiment, the future time interval and/or thresholds are predetermined; for example, the future time interval may be within 8 hours, and the threshold determined based in part on a particular patient context, such as the patient's condition, resources available for caring for the patient, and/or the intensity of care being received by the patient. The determined likelihood may be stored in an electronic health record (EHR) associated with the patient, where it may be used for comparison in a subsequent prediction of an acute inflammatory condition or event.

Based on the determined likelihood, a set of one or more actions may be initiated. One action comprises generating a notification that may be emitted or otherwise communicated to a provider clinician(s) responsible for the care of the patient. In an embodiment, the action comprises generating and emitting or communicating the notification, which may be emitted/communicated via a bedside alarm, user/clinician interface (such as interface 142 described in FIG. 1A), or may be communicated to a smartphone or personal computing device of a caregiver, thereby alerting them of an impending deterioration of the patient's condition. In one embodiment, the notification comprises an event signal and includes the likelihood of future acute inflammatory condition occurrence.

Another action that may be initiated, based on the determined likelihood, comprises a recommendation for modifying a care plan or treatment procedure associated with the patient; for example, a recommendation may comprise increasing patient monitoring or level of care, operating on the patient, or administering a therapeutic intervention, such as a medication or procedure. The recommendation may be provided in conjunction with a notification of the likelihood or a future acute inflammatory condition or event occurrence, and/or may be provided via a user/clinician interface, such as interface 142, described in connection with FIG. 1A.

Yet another action that may be initiated, based on the determined likelihood, comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan, treatment procedure, or therapeutic intervention to be administered to the patient due to the determined likelihood of future acute inflammatory condition or event occurrence. In one instance, the modification comprises changing the executed computer instructions corresponding to monitoring the patient's condition, such as increasing the frequency of obtaining physiological measurements of the patient, or increasing sensitivity of monitoring physiological changes in a patient.

Yet another action that may be initiated, based on the determined likelihood, comprises scheduling healthcare resources for the patient. For example in one embodiment, an operating room (OR) resource may be automatically reserved for the patient, OR staff may be notified and/or automatically scheduled, and transportation/support staff or resources for getting the patient to the OR may be called. In one embodiment, this action comprises modifying or updating a resource/scheduling electronic record in a resource/scheduling system, such as operated as part of a hospital system. In one embodiment, the action comprises, upon a sufficient determined likelihood of a future acute inflammatory condition or event occurrence (wherein significance may be determined using a threshold, as described in method 200 of FIG. 2), initiating a computer instruction that modifies the scheduling healthcare resources, which may include computer instructions for automatically alerting, scheduling, and/or notifying staff, reserving rooms, transportation, or other equipment/space, and which may include changing the priority of the patient (when compared to other patients) for receiving these resources.

As described previously, an aim of embodiments of this disclosure relates to deriving more accurate predictive capabilities (versus conventional computerized-decision support technologies or medical practices) from even moderate-frequency, potentially-aperiodic time series such as that which may be readily obtained with monitoring in acute care environments. Conventional approaches that utilize models derived from time series of measurements generally impose a variety of assumptions regarding the linear properties and stationarity (constancy over time) of the physiologic processes that give rise to the vital signs or hemodynamics time series—assumptions which may not be met for all patients, or may not be met at various times in any particular patient. As a result, model misspecification of non-ignorable effects frequently degrades prediction accuracy, which creates significant drawbacks in the current technology. In view of this, a non-parametric system and method that does not require a priori specification of model structure, such as described herein, is an improvement and is preferable, in particular where such embodiments comprise a non-parametric system or method that is robust against time series non-stationarity and aperiodicity of vital signs measurements, as further described herein. Accordingly, embodiments of the present disclosure determine a qualitative model predicting emergence of an acute inflammatory disorder or event based on catastrophe-theoretic modeling of vital signs time series. Some embodiments comprise a decision support tool, which may in some instances further include a new and specific procedure to be utilized with such a tool, for screening a patient to identify what may be referred to as a catastrophe theoretic biomarker. This "biomarker" is different than a conventional biomarker, such as a mere presence of a substance or chemical in a person that can be directly measured and indicates a particular condition or disease based on its measurement. Rather, this theoretic biomarker is not derived based on a single measurement of a physiological substance, but derived according to a novel catastrophe-theory-based process from a vital signs (or physiological) time-series information, as described herein. However, the catastrophe theoretic biomarker is referred to as a biomarker because, in some embodiments, it may be used in a manner similar to a conventional biomarker; for example, it may be used to indicate a condition or predict a likelihood of developing a condition, such as the emergence of an acute inflammatory disorder.

As further described herein, the catastrophe-theoretic modeling of vital signs time series may be used to determine and communicate a numerical probability of near-term future emergence an acute inflammatory condition, such as sepsis, in patients from whom demographic and physiologic information are acquired, and especially patients in whom prior art diagnostic and prognostic means tend to yield excessive false-negative or false-positive results. Accordingly, the embodiments described herein provide a number of improvements over conventional technologies utilized to detect acute inflammatory disorders including that the embodiments described herein are robust (a) against temporary sensor artifacts or intermittent gaps or failures to perform periodic measurements, (b) against delays in uploading or synchronizing newly acquired patient physiological values with historical vital signs time series measured in the patient, and (c) against non-stationarity in the time series, such as may arise during periods when the patient's health deviates from predominant patterns, due to concomitant health conditions or physiologic phenomena.

Furthermore, the conventional techniques tend to entail concurrent measurement of multiple biomarkers the expression of which is detected by means of Reverse transcription polymerase chain reaction (RT-PCR) and consists of a plurality of markers analytes (such as S100B, CD-11b, CD-14, CD-64, FasL, MCP-1, TNFα, IL-1β, IL-6, IL-8, IL-10, INF-α and INF-γ) that are individually difficult and/or expensive to measure and whose measurement methods involve long turn-around time from the time of specimen collection to the determination of measurement values and estimation of risk or probability. For example, platelet activation markers, including fibrinogen binding to platelets, platelet membrane P-selectin expression, plasma soluble CD40L, and platelet-leukocytes aggregates are assayed by flow cytometry, a time-consuming method requiring equipment and laboratory skills that are not widely available.

Moreover, technologies in the prior art tend to require the utilization of biomarkers that are "exotic" or research-oriented and are not widely available, even in tertiary care facilities in large metropolitan settings. In contrast, a particular advantage of embodiments of the technologies described herein is that they do not require the use of such exotic biomarkers but instead may rely upon routinely-measured vital signs markers.

Additionally, the prior art technologies tend to require utilization of biomarkers whose measurement is sufficiently expensive that their measurement might likely be performed at most once in a given patient's care episode, this circumstance being contrary to the fact that inflammatory conditions and the body's compensatory and defensive reserves fluctuate over time, such that serially-repeated and ongoing re-performance of screening for the presence of inflammatory conditions may be necessary in order for the condition to be detected.

Moreover, due to the expense and logistical issues, the prior art technologies yet further tend to restrict the population who are screened for prediction of possible emergence of inflammatory conditions to just those who already manifest certain acute inflammatory conditions, such as SIRS. Consequently, these conventional approaches fail to detect persons at risk who are not members of those restricted population. In contrast, specific technique(s) and technology utilized by the embodiments described herein avoids such limitations and, thus, further improves upon the decision support technology for detecting acute inflammatory disorders or events because, by way of example and not limitation, such embodiment may result in greater numbers of detections or diagnoses in patients, detection with greater accuracy and/or earlier detection (including predictive detection).

Additionally still, some of the conventional technologies require time series of data that are inconveniently long, such that acute inflammatory processes may be already under way prior to the time when sufficient time series measurements have been obtained. In contrast, embodiments of the technology described herein may use a comparatively short time series of physiological data to produce sensitive and useful detection of emergence of acute inflammatory processes.

Figures 4A, 4B:
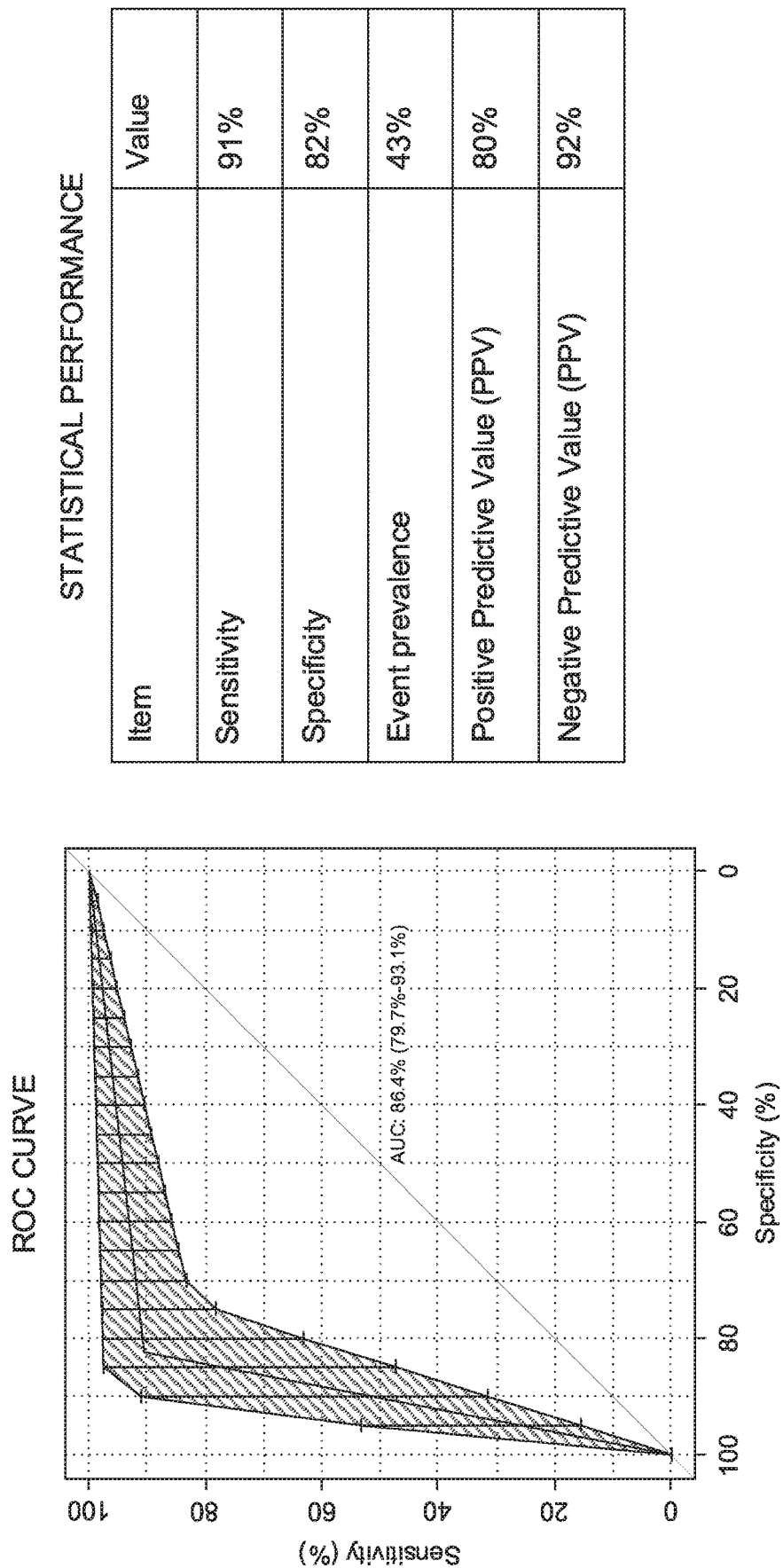
FIGS. 4A and 4B depict statistical performance of an example embodiment of the present disclosure actually reduced to practice, including a receiver operating characteristic (ROC) curve and table of statistical performance metrics indicating an improvement over the conventional technologies.

Yet other conventional approaches that employ vital signs measurements, while simple to use in practice, are able to achieve only a low (35%) statistical sensitivity in detecting or predicting patients who will develop an acute inflammatory disorder. Thus, the resulting false-negative error rate of such prior art technology poses a significant limitation to its utility. In contrast, specific technique(s) and technology utilized by the embodiments described herein substantially overcome this problem. For example, FIGS. 4A and 4B depict measures of statistical performance of one embodiment that was actually reduced to practice, which has a high sensitivity of 91% (which is a 56% improvement in sensitivity over the conventional technology).

As described above, acute inflammatory disorders, including sepsis, are an exceedingly common source of excess morbidity and mortality in acute care. Breathing is maintained and controlled by a network of autonomic neurons in the brainstem that generate respiratory rhythm and receive regulatory inputs. Natural, normal breathing complexity arises from respiratory central pattern generators modulated by peripheral and supra-spinal neural inputs. Bacteremia increases respiratory motor output and dyspnea independent of fever and symptoms. This is primarily due to circulating endotoxin, which alters the autocorrelation of respiratory frequency and reduces the variability and chaotic properties of normal respiration, reducing the complexity of breathing. In sepsis, the autocorrelation coefficient is increased at various lags, and this is reversed by anti-inflammatory medications and by resolution of bacteremia or sepsis. During this process the respiratory rate may or may not be abnormal. However, the inter-relationships of cardiovascular time series and respiratory time series are altered. Embodiments of technology described herein include a novel approach whereby such emerging alterations may be detected in a timely manner in cardiorespiratory patterns that form a "prodrome" that in many instances precedes the onset of systemic inflammatory response syndrome (SIRS) or sepsis.

The development of methods for continuous non-invasive recording of vital signs (which may be embodied as one or more patient monitors, such as monitor 141 described in FIG. 1A) has had a growing impact on the evolution of acute care medicine in such settings outside of critical care units. These devices and methods afford substantial advances in screening hemodynamic status during routine care, and management of intermediate-risk patients who are not sick enough to justify placement in an ICU.

Vital signs monitoring is a prime means by which a patient is evaluated for adequacy of perfusion and oxygenation of the blood, and tracking their level and regulation is thus of great importance to the clinician. In particular, gross alterations of individual vital signs variables, such as heart rate (bradycardia and tachycardia) and blood pressure (hypotension and hypertension) and respiratory rate (tachypnea and bradypnea or hypopnea), are easily detected by the human eye examining a bedside monitor. Alterations of individual vital signs variables are themselves consequent upon many interrelated pathophysiological factors. Some patterns have abruptness of their onset and sharp, deep decrease or increase of the heart rate usually make them identifiable. However, there are many circumstances where no one vital sign variable that is monitored is markedly abnormal, yet the patient does experience an adverse event, such as an acute inflammatory disorder. Likewise, there are many circumstances where patterns of alteration of vital signs emerge slowly, almost imperceptibly, owing to the extensive ability of the organ systems in the body to mount various physiologic compensatory changes to maintain the vital signs values within their normal ranges until at last the body's compensatory reserves have been exhausted. Accordingly, a serious shortcoming in the existing and conventional technologies is that they are unable to reliably detect emergence of an acute inflammatory disorder or event based on monitoring and analyzing vital signs so as to detect an abnormality. (In contrast, embodiments of the disclosure solve this shortcoming in conventional technologies for detecting likely future occurrence of acute inflammation using techniques that are unknown in the industry, as described herein.)

The patterns of interrelationships among heart rate (HR), systolic blood pressure (SBP), and respiratory rate (RR) are complex and diverse. Hemodynamics reflected in these measurements' approximately co-synchronous values can be viewed as a type of nonlinear dynamic system. In order to characterize and predict the behavior of a complex nonlinear dynamic system, nonlinear dynamic theory is utilized. Such theory aims to model the system's different aspects mathematically, yet many simplifications are necessary for a model to be feasible in practice, in near real-time. If the simplifications are reasonable ones, the model may be of considerable use, not only as an embodiment of the system represented and classification of the state that it is presently in, but also for its predictive capabilities regarding probabilities of alternative future states or events that may arise.

Accordingly, one type of nonlinear dynamic theory that can be applied to situations where gradually changing relationships are followed by abrupt changes in behavior is called catastrophe theory. Catastrophe theory is a special sub-field within the broader domain of nonlinear dynamic systems theory. It was introduced by mathematician Rene Thom. Thom criticized classical mathematics (the basis of conventional technologies that may be used for determining acute inflammatory occurrence) for its inability to predict discontinuous processes. He developed methods of determining how slow changes may produce sudden (hence, 'catastrophic') changes in the effects. Catastrophe theory provides mathematically continuous characterizations of discontinuous system behaviors.

A "catastrophe" therefore is a discontinuous change in the behavior, or structure, of a nonlinear dynamic system that occurs as one or a plurality of system parameters is varied. In many dynamic pathophysiological systems, it is possible to see a smooth response under conditions of normal physiologic homeostasis versus a discontinuous response to changes when physiologic compensatory mechanisms have become abnormal or when physiologic reserves have become depleted.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including monitoring, determining, and/or predicting a future occurrence of an acute inflammatory condition or event and additional decision support technology to facilitate caring for patients who may be prone to experience an acute inflammatory event.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer (i.e., computing device) as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example system 200, it is contemplated that in some embodiments functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems; and may be implemented in or as a part of computer system 120. Similarly, EHR system(s) 160 may perform functions for two or more of types of EHR systems (not shown). EHR system(s) 160 also may include records of physiological variables (such as vital signs measurements) obtained via one or more measurement apparati, tests, or screenings, such as measurement device 141.

In some embodiments of the technologies described herein, aspects of a decision support tool for patients having or at risk for an acute inflammatory condition or event occurrence or recurrence may utilize data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor, bedside, laboratory, or in-home patient monitors or sensors, for example, such as measurement device 141.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system(s) 160 directly. For example, in one embodiment a decision support application 140 operating at least in part on a client device (such as a user-operated computer device like a tablet) includes an interface 142 (which may comprise a graphical user interface), which may be used for accessing patient information from an EHR system(s) 160.

An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients to have or develop an acute inflammatory condition or event, which may occur at a future time, and may further include a degree or level characterizing the severity of the condition or event. In some embodiments, application 140 includes or is incorporated into a computerized decision support tool, as described herein. Further, some embodiments of application 140 utilize user/clinician interface 142.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; variables measurements, time series, and predictions (including plotting or displaying the determined outcome and/or issuing an alert) described herein; or other health-related information, and facilitates the display of results, recommendations, or orders, for example. In an embodiment, application 140 also facilitates determining, receiving, or providing: notifications, recommendations, care plan changes, or orders, staffing scheduling, and/or queries from a user, which may be based on the results of monitoring and/or forecasted outputs, and which may in some embodiments utilize user interface 142. Decision-Support application 140 may also be used for providing diagnostic services or evaluation of the performance of various embodiments.

In some embodiments, user/clinician interface 142 may be used with application 140, such as described above. One embodiment of user/clinician interface 142 comprises a user interface that may be used to facilitate access by a user (including a clinician/caregiver such as a medical caregiver, physical therapist, or the like) to a score or prediction determined according to the technologies described herein, including information indicating a likelihood that a patient is experiencing or will experience acute inflammatory condition or event, or other aspects described herein. One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined forecast(s), probabilities (or score), recommendations, scheduling orders, providing instructions (such as measuring, recording, and/or otherwise obtaining vital signs or other physiological variable measurements), confirmations or notifications (such as confirmation that information has been received or notifications that information has not been received and there may be an error in the measuring instrument user operation of a measurement device or measurement procedure), reminders (such as notifications to obtain a physiological measurement sample), or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for facilitating diagnostic services or evaluation of the performance of various embodiments.

Example operating environment 100 includes measurement device 141 communicatively coupled through network 175 to an EHR system 160. In an embodiment, measurement device 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient, and which may be acquired periodically, continuously, as needed, or as they become available, and may be represented as one or more time series of measured variables. In one embodiment, measurement device 141 comprises sensors for obtaining (and in some instances pre-processing or interpreting) non-invasive recording of vital signs, which may be obtained continuously, periodically, or at irregular intervals. Accordingly, the term measurement is used broadly herein, and it is contemplated that in some embodiments, measurement device 141 may not perform measurement but may receive information about physiological parameters (such as heart rate (HR), blood pressure (e.g., systolic blood pressure or SBP), respiratory rate (RR), for example and without limitation) which may be measured, observed, or otherwise recorded. Some embodiments of measurement device 141 may comprise one or more sensors, an interface component, and/or processing/communications component (not shown). In some embodiments, measurement device 141 may comprise a patient monitoring system such as Sotera ViSi®, Finapres® NOVA™, or Covidien ZephyrLIFE™. In some embodiments, measurement device 141 may include a Bluetooth or wireless communication data-transfer capability and may be wirelessly communicatively coupled with an application on a computing device, such as a smartphone an app or aspect of decision support application 140. In some embodiments, measurement device 141 comprises patient bedside monitor, such used in hospital. In an embodiment, one or more sensor components of measurement device 141 may comprise a user-wearable sensor component or sensor component integrated into the patient's environment. Examples of sensor components of measurement device 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the invention disclosed herein may be received from human measurements, human observations, or automatically determined by sensors in proximity to the patient. For example, in one embodiment, a nurse periodically measures a patients' blood pressure and enters the measurement and/or observations via user/clinician interface 142. In another example, a nurse or caregiver enters one or more progress notes for an in-patient via user/clinician interface 142. Similarly, values for other vital signs variables may be entered via user/clinician interface 142.

Examples of physiological variables monitored by measurement device 141 can include vital signs variables, such as heart rate (bradycardia and tachycardia) and blood pressure (hypotension and hypertension), oxygen saturation (peripheral desaturation), or other vital signs as described herein. In some embodiments physiological variables monitored by measurement device 141 may include any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient in order to facilitate clinical decision making In an embodiment, a measurement device 141 comprises a sensor probe and a communication link that periodically transmits identification information and probe data to a decision support application 140, so that the time series of monitored values is stored in a record associated with the patient on an EHR system 160, thereby enabling the decision support application 140 to form a raw binary alarm indication and/or a physiological variable decision statistic.

Embodiments of measurement device 141 may store user-derived data locally or communicate data over network 175 to be stored remotely. Some embodiments of measurement device 141 include a monitor interface, which may be embodied as I/O such as buttons and sounds emitted from the measurement device 141, its firmware or software application or app operating on a user's mobile device or computer system 120, and in an embodiment may facilitate uploading of measured (or recorded, or otherwise received) information from measurement device 141 to computer system 120. Additionally, some embodiments of measurement device 141 include functionality for processing user-derived information locally or for communicating the information to computer system 120, where it is processed. In some embodiments, the processing may be carried out or facilitated by one or more software agents, as described below. In some embodiments the processing functionality, performed on measurement device 141 and/or computer system 120 includes pre-processing and/or signal conditioning, such as removing noise or erroneous information.

Example operating environment 100 further includes computer system 120, which may take the form of one or more servers, and which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140 or interface 142 may operate on or utilize computer system 120. Similarly, a portion of computing system 120 may be embodied on user interface 142, application 140, and/or EHR system(s) 160. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

In embodiments, model variables indexing (or mapping) service 122 facilitate retrieving patient physiological variables, which may include frequent item sets, extracting database records, and/or cleaning the values of variables in records. For example, service 122 may perform functions for synonymic discovery, indexing or mapping variables in records, or mapping disparate health systems' ontologies, such as determining that a particular medication frequency of a first record system is the same as another record system. Predictive models service 124 in general is responsible for providing multi-variable models for predicting near-term occurrence of an acute inflammatory condition or event, such as the linear and cusp catastrophe models described in connection to method 200 of FIG. 2. In some embodiments, services 122 and 124 may invoke computation services 126.

Computation services 126 may perform statistical software operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services. In an embodiment, computation services 126 and predictive models service 124 include the services or routines, which may be embodied as one or more software agents or routines such as the example embodiments of computer program routine illustratively provided in FIG. 5. In one embodiment, computation services 126 comprises the R-System cusp package for cusp-catastrophe modeling and model fitting, which is invoked in the example computer program routines shown in FIG. 5.

Computation services 126 also may include natural language processing services (not shown) such as Discern nCode™ developed by Cerner Corporation, or similar services. In an embodiment, computation services 126 include the services or routines, which may be embodied as one or more software agents or computer software routines such as the example embodiments of computer program routines illustratively provided in FIGS. 5 and 6. Computation services 126 also may include services or routines for utilizing one or more prediction models such as described in connection to FIG. 2 and the example computer program routines illustratively provided in FIG. 5. In some embodiments, computation services 126 use EHR system(s) 160, model data and model storage services (not shown), and/or other components of example operating environment 100, and may also include services to facilitate receiving and/or pre-processing physiological data. For instance, model data and model storage services may be utilized to perform services for facilitating storage, retrieval, and implementation of the forecasting models described herein and of the data used in the models.

In some embodiments, stack 125 includes file system or cloud-services 128. Some embodiments of component 128 may comprise an Apache Hadoop and Hbase framework, or similar frameworks operable for providing a distributed file system, and which in some embodiments facilitate provide access to cloud-based services, such as those provided by Cerner Healthe Intent®. Additionally, some embodiments of file system or cloud-services 128 or embodiments of stack 125 may comprise one or more stream processing service(s). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
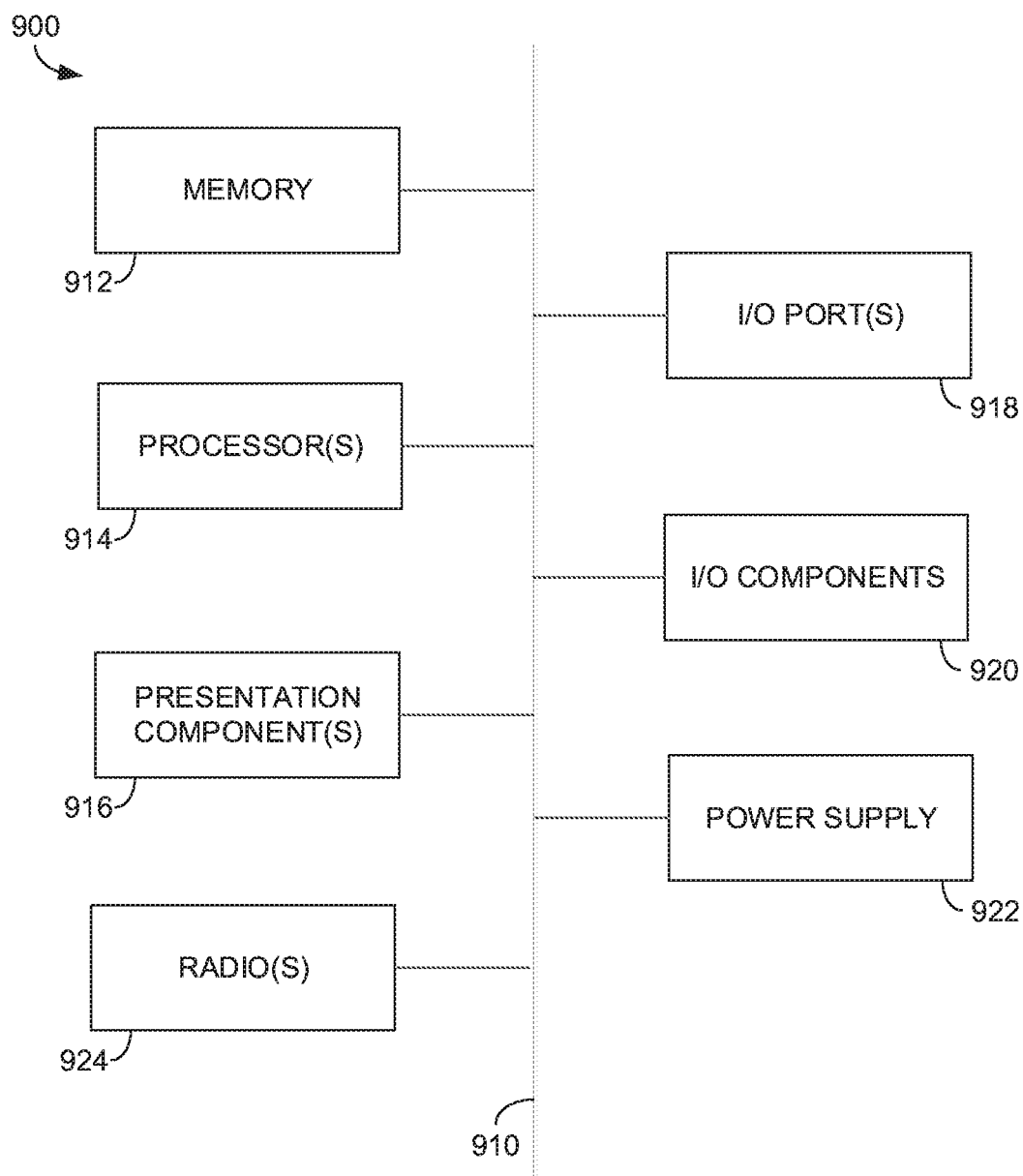

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. In an embodiment, storage 121 is embodied as memory 912. Presentation component(s) 916 present data indications to a user or other device. Exemplary presentation components include a display device, speaker, printing component, vibrating component, etc. In an embodiment, functionality provided via user/clinician interface 142 is facilitated by one or more presentation components 916.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
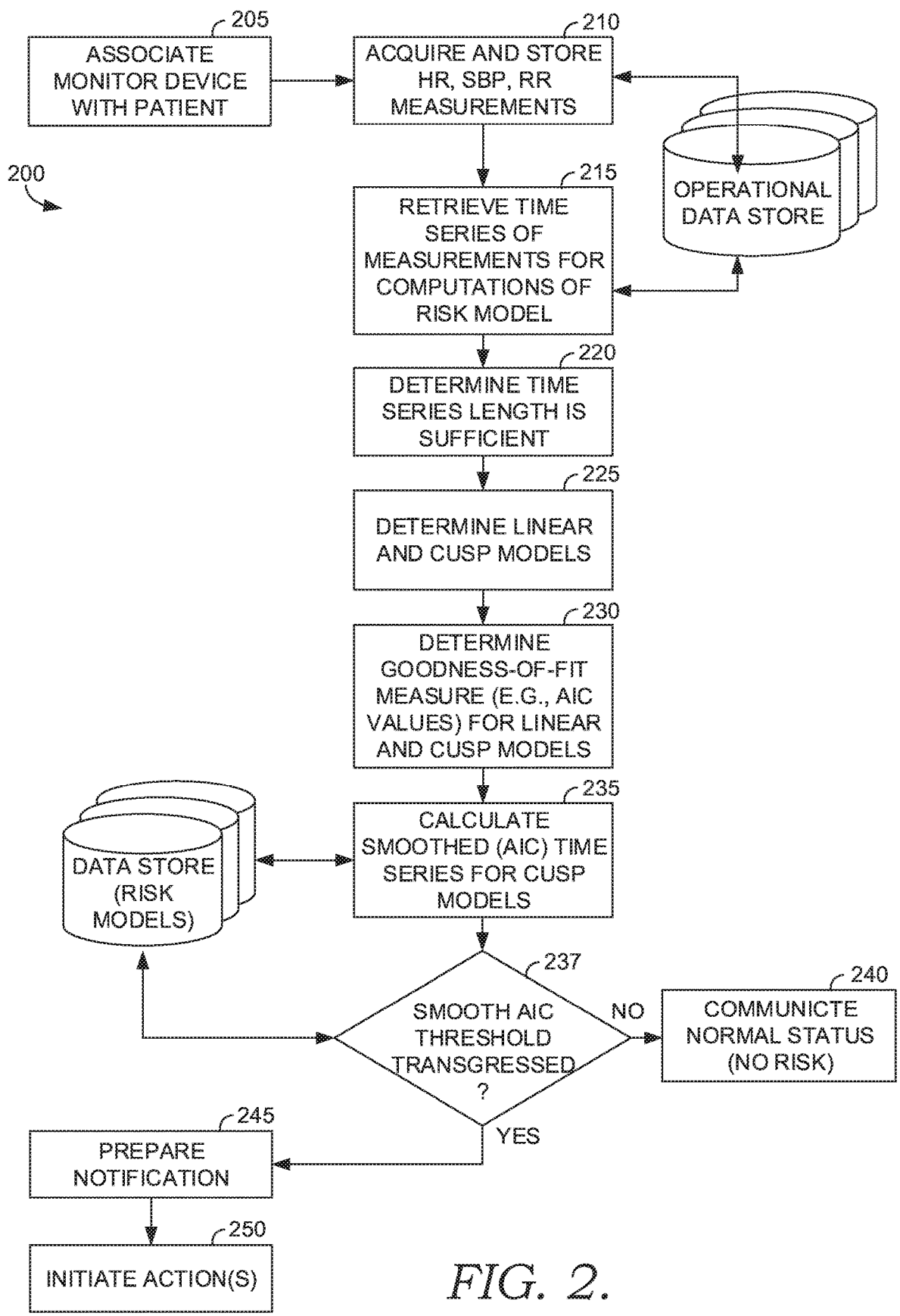
FIG. 2 depicts a flow diagram of a method for predicting emergence of the acute inflammatory disorder or event for a human patient within a future time interval, in accordance with an embodiment of the disclosure.
Figure 3B:
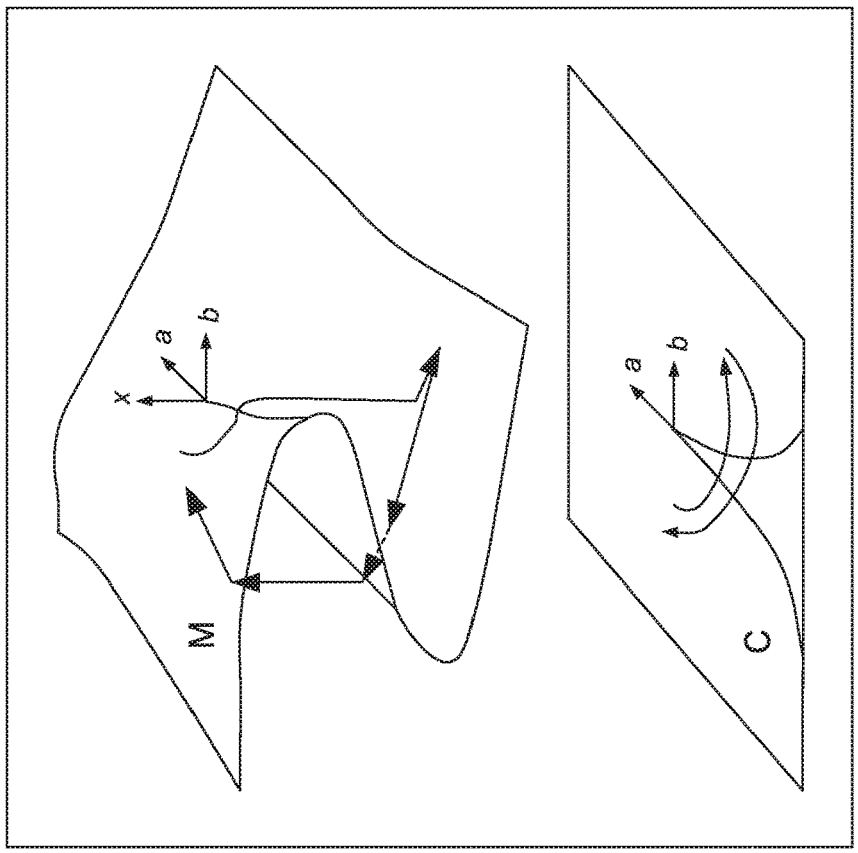
FIGS. 3A-3E each depict an illustrative example of a positive case wherein near-term future events were preceded by multivariable relationships that were better modeled by cusp catastrophe model than by a linear model, in accordance with an embodiment of the disclosure.
Figure 3A:
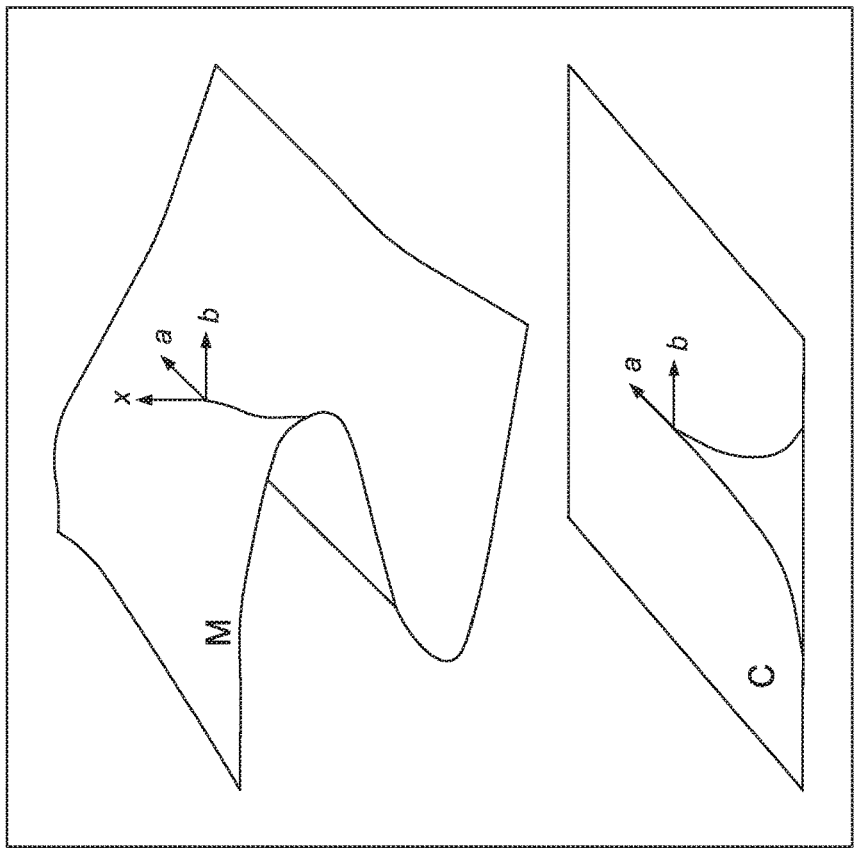
Figure 3D:
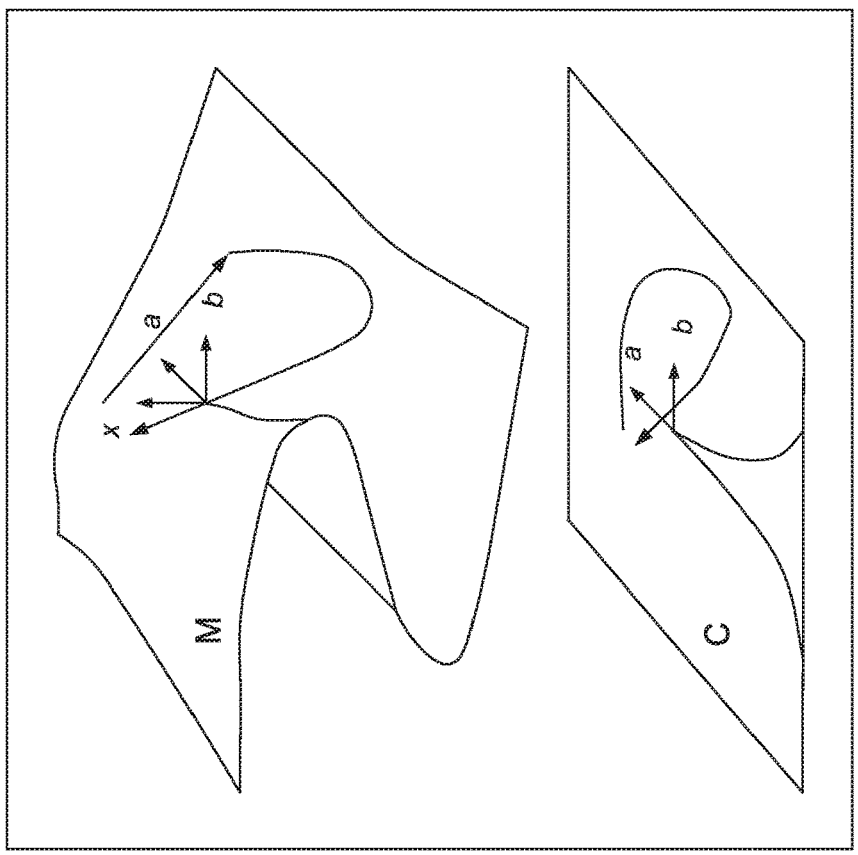
Figure 3C:
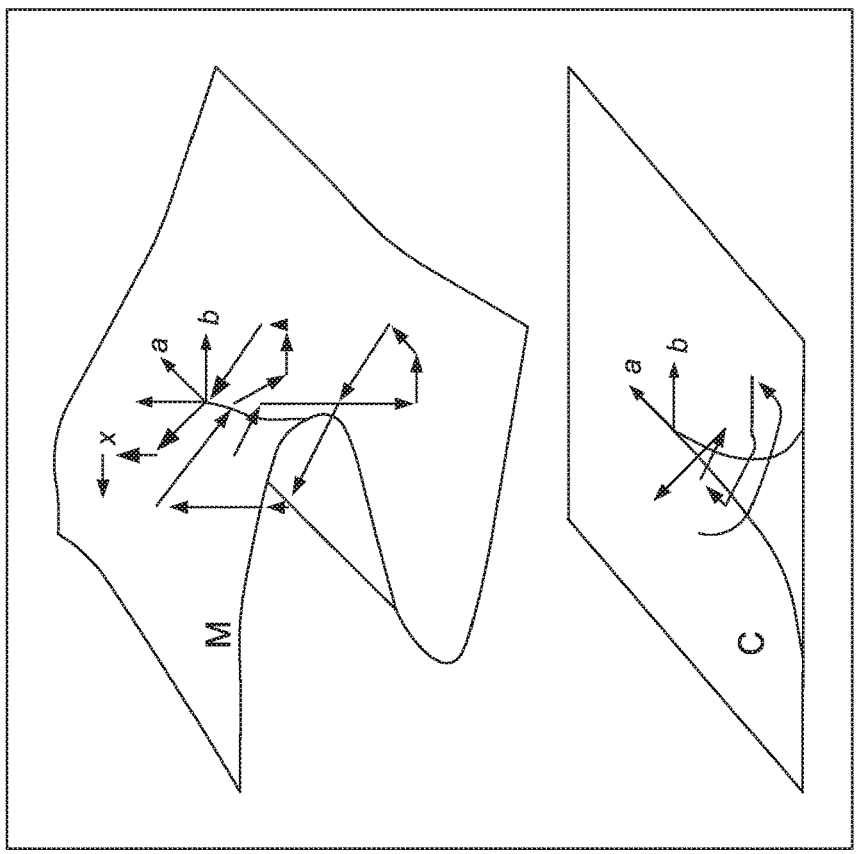
Figure 3E:
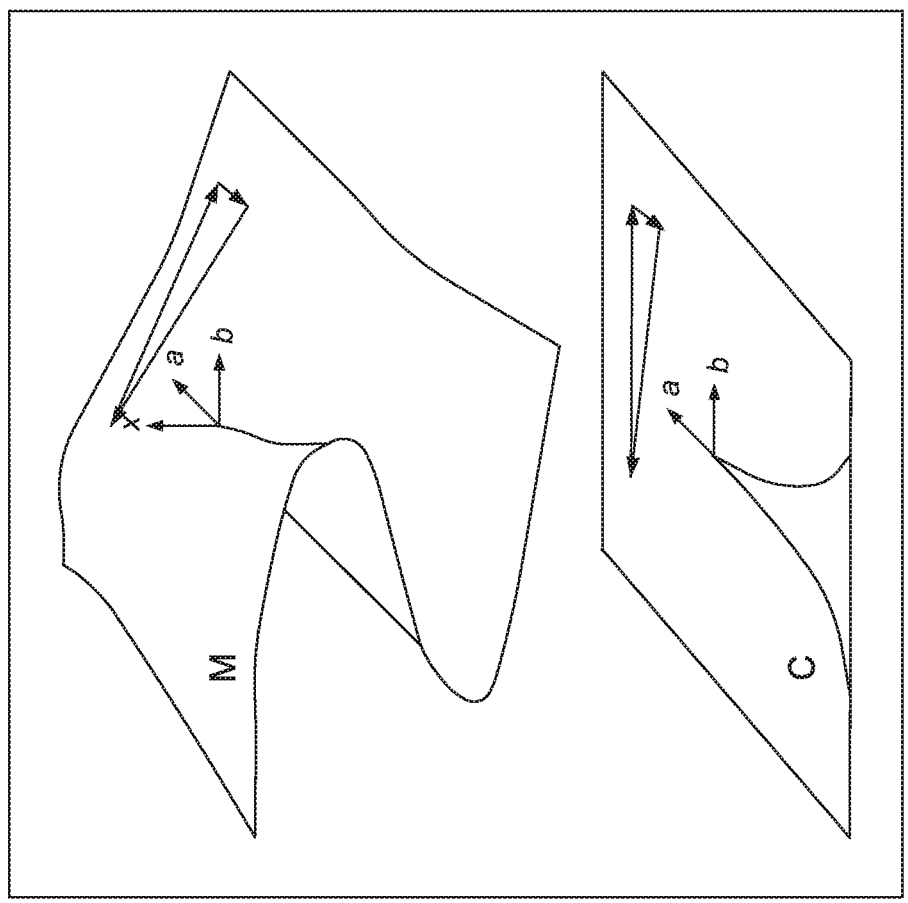

Turning now to FIG. 2, one example embodiment of a method for predicting an occurrence of an acute inflammatory condition or event for a human patient within a future time interval is provided, and referred to generally as method 200. In particular, example method 200 utilizes catastrophe-theoretic approach for determining the probability of an acute inflammatory event. As described previously, a catastrophe may be understood as a discontinuous change in the behavior, or structure, of a nonlinear dynamic system that occurs as one or a plurality of system parameters is varied. In some embodiments, aspects of method 200 may be carried out using the example computer program routine depicted in FIG. 5.

With reference to FIG. 2 and method 200, generally, in catastrophe theory, the phenomenon under study is assumed to be governed by a potential function, V. Stable states of the system may be regarded as minima of the function V. If the potential function has multiple minima, then more than one stable state may be accessible to the system at a particular time. Changing the control parameters may alter the form of the governing potential function so as to change the positions, relative heights, or total number of local minima Thus, the observed state of a system may change in a discontinuous way as the controls are changed. The observed discontinuous changes in state are called catastrophes. A central proposition of catastrophe theory is the classification theorem, which states that, given a maximum of four control parameters which may themselves be composite variables comprised of a plurality of other variables, all discontinuous changes of events in a nonlinear system can be modeled by one of seven elementary topological types, each with a unique shape and set of mathematical properties. One of these includes cusp catastrophe.

Cusp Catastrophe. Turning briefly to FIGS. 3A-E, examples of cusp-type catastrophes are depicted. In particular, FIGS. 3A-3E show a plot of a curved surface with a pleat, called the system behavior surface, M, above a planar surface, C, over which two control factors vary. Mathematically, a cusp catastrophe is associated with a potential function of the form $V(x; a, b) = \frac{1}{4} x^4 + \frac{1}{2} ax^2 + bx$, where a and b are the control factors and x is the variable whose behavior is plotted on the behavior surface. The topological feature of the behavior surface represents the graph of all points where the first derivative of this function is equal to zero.

This catastrophe surface arises from consideration of extrema (particularly minima) of the potential. The first derivative of the cusp function is $\partial V(x; a, b)/\partial x = x^3 + ax + b$. The glimpse at the mathematical foundation of the theory given here is meant to demonstrate that the graphic representations of the cusp catastrophe in the present invention are not arbitrary configurations or ex post facto constructions. In particular, when plotting the behavior surface, most combinations of control factors a and b result in a unique solution for setting the derivative equal to zero. These unique solutions are points of stable equilibrium or the most likely mode of behavior for the particular combination of control factors. The set of these points represents the areas that define the stable, non-pleated part of the behavior surface.

But for some combinations of control factors there are multiple stable equilibria, and multiple modes of behavior. Thus, in the middle of the plot the M surface folds upon itself and overlaps, and makes a continuous pleated surface with a 'cusp' where the pleat is. The cusp or pleated part represents unstable equilibria and points on this surface region are generally inaccessible to the system. Variation in the control factors in the area of the pleat will shift the behavioral variable between the upper and lower stable surfaces on M. Even though the changes in the control variables are continuous and smooth, as reflected by the smooth continuity of the pleated surface, small changes in their relative levels cause sudden, discontinuous changes in the system's behavior. The discontinuous jump between stable surfaces is a catastrophe. Both smooth and catastrophic change can occur with a cusp catastrophe model.

Catastrophe Flags. There are five inter-related qualitative features or 'flags' that can be associated with a catastrophe surface. These five catastrophe flags are effective for determining the presence or absence of a catastrophe-type nonlinearity behavior of the system from which the data represented on the surface originate.

Modality. This means that the system has two or more distinct states that may exist. In other words, the potential describing the system has more than one local minimum for some range of the external control parameters. The cusp catastrophe becomes bimodal when the control parameters lie within the cusp-shaped region.

Inaccessibility. This means that the system has an equilibrium state which is unstable. Such equilibria are unstable because infinitesimal perturbations exist which decrease the value of the potential function V. Whenever the potential V has more than one local minimum, it must have at least one unstable equilibrium. The two sheets over the cusp-shaped region, representing the locally stable minima, are separated by the pleated region, representing an unstable local maximum.

Sudden Jumps. A small change in the value(s) of one or more control parameters may result in a large change (sudden jump) in the value of the state variable as the system jumps from one local minimum to another. The transition from the neighborhood of one local minimum to another represents a large change in the value of the behavior state variable, which often occurs on a fairly rapid time scale. A sudden jump in the value of the state variable occurs as the system state jumps from a region on one side of the cusp catastrophe manifold to the other.

Divergence. Usually a small perturbation in the values of the control parameters will lead to only a small change in the initial and final values of the state variables. However, in the neighborhood of the cusp, small changes in the control parameter's initial values may lead to large changes in the state variable's subsequent values. The instability of processes against perturbation of the control parameter trajectory is called divergence.

Hysteresis. This occurs whenever a process is not strictly reversible. That is, the jump from one local minimum 'A' to a different local minimum 'B' does not occur over the same point in control parameter space as the jump transiting in the other direction, from local minimum 'B' to local minimum 'A'. For the cusp catastrophe, hysteresis occurs when the jump from one sheet to another does not occur for the same values of the control parameters as the reciprocal jump.

Any one or more of these five catastrophe flags suggest or indicate the presence of a catastrophe-type discontinuity.

Catastrophe theoretic models describe hemodynamic abnormalities that are prodromic to acute inflammatory disorders as an abrupt response to changing physiological compensation. Because of its three-dimensionality and topological features, the cusp catastrophe model provides a qualitatively consistent characterization of vital signs variables' interrelationships. The smooth fold curve or pleat connecting the two surfaces implies that the variables regulating the change between patterns act in a continuous fashion even though the switch from one pattern to the other is discontinuous. It is this qualitative characteristic of vital signs time series patterns that immediately precede the onset of an acute inflammatory disorder that results in such time series' being well-fit by a catastrophe model. Whenever continuously changing control parameters have an abruptly changing effect, the process may be well represented by a catastrophe model.

The fundamental theorems of catastrophe theory do not require an explicit knowledge of the potential V; they may apply generically to all smooth (mathematically differentiable) potential functions. Provided there is a good reason to believe that the dynamics of a system (vital signs and hemodynamics variables, as in the context of embodiments described herein) is such that it tends to minimize some smooth function V(x; a, b) that depends on two parameters, as here, then a cusp-type catastrophe is likely. The validity of this approach is independent of our knowledge of the manner in which V is minimized A main feature of the modeling process(es) in embodiments of this disclosure in this regard is the assumption of the existence of such a potential. The important point is not whether a given equilibrium is stable or not, but whether it persists over moderate intervals of time as physiologic compensations, or therapeutic and preventive maneuvers, or other factors in the system change.

Accordingly and in light of the foregoing, method 200 begins at step 205, wherein a monitor device, such as measuring device 141, is associated with the patient. In one embodiment, step 205 comprises physically attaching a patient to the device and/or associating a monitor-device identifier (ID) with the patient, such that patient data acquired via the device is associated with the patient. In one embodiment, a patient account or patient EHR is associated with the monitor.

At step 210, vital sign (or physiological) variables are acquired for the patient. In one embodiment, these variables comprise of heart rate (HR), systolic blood pressure (SBP), and respiratory rate (RR) measurements, which may be acquired using the monitor, such as by using one or more measurement devices 141. Embodiments of step 210 may acquire the vital signs measurements continuously, periodically, or at non-regular intervals. The measured variables may be stored in a data store, such as storage 121, and may be stored on an EHR system(s) 160 in a record associated with the patient. In some embodiments, the date/time information for the measurements is stored with the measured variable values such that a time series may be determined.

At step 215, the historical measurements of the patient's vital signs are retrieved and a time series is determined. The time series may be constructed by appending the most recent vital signs measurements to the historical measurements, using the associated date-time information. In some embodiments, the historical measurements comprise measurements obtained within a recent timeframe such as the previous several hours, last 4 hours, last 12 hours, or previous 1-3 days. In some such embodiments, only historical measurements from within this recent timeframe are retrieved and used for the constructing time series.

At step 220, the time series may be evaluated to determine whether it is of sufficient length. In an embodiment, where the time series is determined to be greater than a pre-determined length, method 200 proceeds to step 225. But if the time series is not long enough, then method 200 returns to step 210, where additional vital signs measurements may be acquired. In one embodiment, the pre-determined length comprises 40 samples (which may correspond to 40 serial vital signs measurements), and in another embodiment, the pre-determined length comprises 50 samples or 100 samples or more, which may provide a more accurate or earlier detection. In one embodiment, step 220 further comprises determining that the measurements are of a sufficiently minimum frequency, such as measurements obtain on the order of every few seconds or several times per minute. Further still, in some embodiments, step 220 (or of method 200, prior to step 225), may standardize and center each of the variables' time series values.

At step 225, linear and cusp models are determined. Embodiments of step 225 may determine the linear and cusp models based on a boxcar of the time series comprising N recent samples. In one embodiment comprises approximately 50 samples, and in another embodiment, N comprises approximately 100 to 500 samples, which may provide greater accuracy and/or earlier detection. An example embodiment of step 225 is illustratively provided in the computer program routine shown in FIG. 5. This example embodiment uses the cusp package (computation services 126, in FIG. 1A) of the R-system.

At step 230, a goodness-of-fit measure may be determined for the linear and cusp models. In one embodiment, step 230 comprises determining Akailke Information Criterion (AIC) values for the linear and cusp models. AIC represents a measure of the relative quality of statistical models for a given set of data. Thus, for a collection of models for the data, AIC estimates the quality of each model, relative to each of the other models. Hence, AIC may be used as a means for model selection. In another embodiment of step 230, a Bayesian Information Criterion (BIC), or other suitable criterion may be determined. In further embodiments, Cobb's maximum likelihood method and the maximum likelihood method for linear modeling may be used.

At step 235, the time series may be smoothed for the cusp model(s). Embodiments of step 235 may perform a de-noise operation on the AIC (or BIC) time series, which may be implemented using a low-pass filter. In this way, the likelihood of false alarms may be reduced. However, the smoothing applied at step 235 is not so great that detection of the acute inflammatory event is delayed until it is impending. One embodiment of step 235 comprises using a Hanning filter (Hanning window), which may be configured to approximately five to seven points. In one embodiment, Exponentially-Weighted Moving Average (EWMA) is used to determine the smoothed time series of the AIC values.

At step 237, it is determined whether the smoothed time series threshold is transgressed. Embodiments of step 237 may thus determine the classification or probability of future acute inflammatory condition occurrence within the defined future time interval based on whether the smoothed cusp model AIC threshold is transgressed or, alternately, based on whether a threshold for the ratio of linear-to-cusp model AIC values is exceeded. Where the threshold is transgressed, exceeded (or otherwise satisfied), method 200 proceeds to step 245; but where the threshold is not satisfied, then method 200 proceeds to step 240.

In embodiments of step 237, the threshold may be predetermined and may be context-dependent. The threshold is determined empirically, in an embodiment, and may be set according to a table (or function) for a particular context, such as the patient condition, available resources for patient care, and/or the intensity of care. For example, in one embodiment, the threshold may be based on healthcare resources such as staffing or level of care already being received by the patient. Thus, where the patient is already receiving active care and monitoring, such as in a surgical ICU, a higher threshold may be used such that exceeding (or satisfying) the threshold could lead to paging (or notifying) the surgeon and may also lead to taking the patient back to the OR. But a lower threshold may be used where a patient is, say, in a labor and delivery unit (e.g. a birthing suite) following post-partum hemorrhage, and not presently receiving a high level of care.

At step 240, where the threshold is not exceeded or satisfied, method 200 may end, or may otherwise report that the patient is not at risk for an acute inflammatory condition or event within a future time horizon. At step 245, where the threshold in step 237 has been satisfied and thus a significant risk for an acute inflammatory condition exists, a notification of the determined risk, such as described previously, may be generated. Some embodiments of step 245 may comprise storing the result of the determination in an electronic health record (EHR) associated with the patient, and further, may include providing the patient's EHR (or facilitating access to the EHR) in the notification. In some embodiments, step 245 may be part of step 250.

At step 250, based on the determined likelihood, a set of one or more actions may be initiated in response to determining significant risk of an acute inflammatory condition. For example, as described herein, a notification may be generated and emitted or otherwise communicated to a provider clinician(s) responsible for the care of the patient; a recommendation for modifying a care plan or treatment procedure associated with the patient may be generated and provided; computer code executed in a healthcare software program for treating the patient, may be modified, thereby transforming the program at runtime; healthcare resources may be scheduled or arranged; or other actions may be initiated in response to the determined risk. In some embodiments, a communication can be provided to an attending caregiver indicating a change in patient condition that warrants attention by the caregiver. In some embodiments, a patient's health record is updated to include the state of the patient's health, as determined by the clinical decision support system. For example and not limitation, a patient's health record can be updated to include an indication of the patient's risk. In some aspects, this may be an indication that the patient is at a low, moderate, or high risk. In some embodiments, the clinical decision support system can trigger an audible or visual indication that communicates that a patient is at risk, thereby resulting in a caregiver attending to the patient. In some embodiments, the initiated actions may be based on the level of risk (i.e. the probability that an acute inflammatory event will occur, such as a high or moderate likelihood), and/or how impending the event is likely to occur (e.g. how far into the future time interval, which may provide a sense of urgency). Some embodiments of the steps of method 200 may be carried out using the example computer program routine depicted in FIG. 5. Additionally, in some embodiments, method 200 may utilize Cobb's maximum likelihood method and the maximum likelihood method for linear modeling.

Example Reduction to Practice

With reference to FIGS. 4A-B, and 5-6 and continuing reference to method 200 of FIG. 2 and FIGS. 3A-3E, an example is provided of an embodiment of the disclosure constructively reduced to practice. This reduction to practice is provided in part to demonstrate the improvement to technology that is achieved by employing the embodiments described herein. Here, computer system 120 running the Linux operating system (129) was utilized with the open-source statistical software package R, and the R module cusp (Computation services 126). This example embodiment used the example computer program routine provided in FIG. 5.

In this example embodiment, an observational study was performed using a consented, secondary-use-rights-granted data set. Illustrative series of vital signs (approximately co-synchronous HR, SBP, and RR measurements) values were retrieved from a subset of persons admitted to hospital, whose de-identified, confidentiality-protected health records were stored and maintained in Cerner's Health Facts® data warehouse. The cohort selected was comprised of 606,097 hospital in-patients who developed sepsis, for whom Health Facts® contained at least 50 serial vital signs values measured over a period of not less than 4 hours. Positive cases in this cohort were patients who experienced an in-hospital emergence of sepsis. Negative controls (N=607,102) were in-patients who did not experience sepsis while in-hospital, ascertained by the absence of standard sepsis clinical and laboratory criteria, a uniform set of definitions for states associated with the sepsis syndrome was used.

Systemic inflammatory response syndrome or SIRS is considered the accepted term for a clinical state in which two or more of the following clinical parameters are present: body temperature>38° C. or <36° C.; heart rate>90 beats/minute; respiratory rate>20 breaths/minute, or a $PCO_2$<32 mm Hg; and white blood cell count>12,000/mm3, <4000/mm3, or having >10% immature band forms. Sepsis is understood to be SIRS with a confirmed infectious process (positive culture). Severe sepsis is sepsis associated with organ dysfunction, hypoperfusion abnormalities, or hypotension. Hypoperfusion abnormalities include, but are not limited to, lactic acidosis, oliguria and mental status changes. Septic shock is understood to be sepsis-induced hypotension resistant to fluid resuscitation, and, having, in addition, the presence of hypoperfusion abnormalities. FIGS. 4A and 4B depict statistical performance achieved by this example embodiment actually reduced to practice, including a receiver operating characteristic (ROC) curve (FIG. 4A) and table of statistical performance metrics (FIG. 4B) indicating an improvement over the conventional technologies. The ROC curve can be generated based on a computer program routine illustrated in FIG. 6.

It should be appreciated that conventional technologies have not been able to achieve this outcome. As one skilled in the art would recognize, the accuracy of the instant technology exceeds that of conventional technology. As described herein, conventional industry practice is generally capable of achieving 35% sensitive in detecting an acute inflammatory disorder. In contrast, embodiments described herein offer a 91% sensitive. As should be appreciated, this 56% improvement has a profound impact on saving patients' lives.

In addition to offering an improved accuracy over conventional technology, embodiments described herein offer an improved accuracy without the use of expensive laboratory tests or machinery required in the conventional industry practice. As such, hospitals and other care providers can utilize the technology described herein without investing in additional laboratory resources or specific machinery.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

Embodiment 1. A system for forecasting emergence of an acute inflammatory disorder in a patient comprising: a) an input means for entering vital signs values representative of heart rate (HR), systolic blood pressure (SBP), and respiratory rate (HR) of the patient at time t; b) a first calculation means for deriving the multiplicative rate-pressure-product (RPP) from said HR and SBP measurements if the RPP is not separately provided by the input means; c) a memory means for storing a time series of said vital signs values; d) a processor connected to said input means and said memory means for determining whether a linear model or a cusp catastrophe-theoretic model better accounts for the variation in the time series; e) a criterion of the statistical goodness-of-fit of said models, such as the Akaike Information Criterion (AIC), whereby the models' adequacy may be compared quantitatively; f) a second calculation means whereby successive values of said criterion of model performance may be assembled into time series; g) a third calculation means for smoothing the model performance criterion time series; h) a fourth calculation means for determining whether persistence of abnormal values of the criterion time series are sufficient to establish significantly elevated risk of an acute inflammatory disorder or events in the patient and sufficient to merit emitting an alarm pertaining to said elevated risk; i) a display means connected to said processor for displaying predicted events; j) a memory means for storing the event predictions and their associated date-time coordinates; k) a database memory means for storing and logging notifications, such as alarms, for forecasting emergence of acute inflammatory disorders that the user may note of, toward preventing or mitigating the severity of subsequent acute inflammatory disorders; and l) a means for communicating said notifications.

Embodiment 2. The system of embodiment of 1, wherein said memory means includes means for storing time series values of the goodness-of-fit criterion and of the alarm status.

Embodiment 3. The system of embodiment of 1, wherein fitting the time series data is performed by Cobb's maximum likelihood method for cusp-catastrophe modeling and by a maximum likelihood method for linear modeling.

Embodiment 4. The system of embodiment of 1, further comprising a communication means connected to said processor for establishing a communication link between said apparatus and a healthcare provider computer and for transmitting and receiving data therebetween.

Embodiment 5. The system of embodiment of 4, wherein said communication means comprises a modem means for establishing said communication link through a communication network.

Embodiment 6. The system of embodiment of 4, wherein said communication means comprises an input/output port for establishing said communication link through a connection cord.

Embodiment 7. The system of embodiment of 1, wherein the fourth calculation means further includes a means for determining transgressions of a reference range for the smoothed goodness-of-fit metrics time series, thereby determining the near-term risk of an acute inflammatory disorder, such as SIRS or sepsis.

Embodiment 8. A method for forecasting an acute inflammatory condition in a patient, comprising: acquiring one or more vital signs values to determine a time series; generating a linear model and a cusp catastrophe model based on the determined time series; quantitatively evaluating the linear model and the cusp catastrophe model to determine which model better accounts for the variation in the time series; determining a performance criterion time series by selecting the model that better accounts for the variation in the time series; evaluating the performance criterion time series using a threshold; based on satisfying a threshold, determining an elevated risk of an acute inflammatory event for the patient; and based on the determined risk, initiating a response action to treat the patient or mitigate the determined risk.

Embodiment 9. The method of embodiment of 8, wherein the cusp catastrophe model is based on one or more vital signs variables or composite variables derived from raw vital signs variables.

Embodiment 10. The method of embodiment of 8, wherein the cusp catastrophe model potential is based on a rate-pressure-product (RPP).

Embodiment 11. The method of embodiment of 8, wherein the cusp catastrophe model uses an asymmetry function that comprises a multivariable function based on heart rate (HR) and systolic blood pressure (SBP).

Embodiment 12. The method of embodiment of 8, wherein the cusp catastrophe model uses a bifurcation function comprising a multivariable function of heart rate (HR) and respiratory rate (RR).

Embodiment 13. The method of embodiment of 8, wherein cusp catastrophe modeling is performed on subsets of the measurements of the time series, such that each subset is comprised of a plurality of approximately co-synchronous measurements, preferably not less than 100 time points and not more than 1,000 time points.

Embodiment 14. The method of embodiment of 8, wherein the acquisition of the vital signs data is performed with a frequency not less than once per minute, preferably at least once per 15 seconds, or more preferably at least once per 5 seconds.

Embodiment 15. The method of embodiment of 8, wherein intermittent sensor error or artifact or signal dropout or other causes of missingness of individual instances of HR, SBP, and RR measurements affect not more than 10% of the values in a time series.

Embodiment 16. The method of embodiment of 8, wherein the time series of each vital signs variable is standardized.

Embodiment 16. The method of embodiment of 15, wherein the standardization comprises scaling the vital signs variable to have standard deviation=1.0 and centered to have mean=0.0.

Embodiment 18. The method of embodiment of 8, wherein vital signs measurements are transformed, standardized, or inverted, so that positive extremal scaled, centered values are abnormal and negative values correspond to RR measurements in a normal range.

Embodiment 19. The method of embodiment of 8, wherein the determination of comparative goodness-of-fit of cusp versus linear models is represented by the 'linear-to-cusp model information criterion ratio' of the respective models' Akaike Information Criterion (AIC) values or Bayesian Information Criterion (BIC) values or similar goodness-of-fit measures as are known to those practiced in the art.

Embodiment 20. The method of embodiment of 8, wherein the inflammatory condition is one of the group consisting essentially of: systemic inflammatory response syndrome, sepsis, severe sepsis, and septic shock.

What is claimed is:

1. Computer storage media having computer-executable instructions embodied thereon that when executed, provide a decision support system for predicting emergence of an acute inflammatory condition, the computer-executable instructions comprising:
    acquiring, using one or more patient monitors, a plurality of measurements of vital signs for a patient, the plurality of measurements of vital signs acquired over a timespan;
    constructing, within the computer storage media, a vital signs time series using the acquired plurality of measurements of vital signs;
    determining, via a computer processor, a linear model and a cusp catastrophe model based on the vital signs time series;
    determining, via the computer processor, a goodness-of-fit measure for the linear model and the cusp catastrophe model;
    determining, via the computer processor, a likelihood of the patient experiencing an occurrence of an acute inflammatory condition over a future timeframe by determining that Akaike Information Criterion (AIC) values for the cusp catastrophe model exceeds a first threshold; and
    based on the determined likelihood, automatically modifying a computer code executed in a healthcare software program for treating the patient, thereby transforming the healthcare software program.

2. The media of claim 1, wherein the plurality of measurements of vital signs comprise values representative of a heart rate (HR), a systolic blood pressure (SBP), and a respiratory rate (RR).

3. The media of claim 1, wherein the cusp catastrophe model is based on an asymmetry function, the asymmetry function comprising a heart rate (HR) and a systolic blood pressure (SBP).

4. The media of claim 1, wherein calculating the goodness-of-fit measure comprises determining the AIC values the linear model and the cusp catastrophe model.

5. The media of claim 4, further comprising determining a smoothed AIC time series for the cusp catastrophe model.

6. The media of claim 5, wherein the smoothed AIC time series is determined using an Exponentially-Weighted Moving Average (EWMA) operation.

7. The media of claim 1, wherein automatically modifying computer code comprises one or more of: automatically generating and communicating an electronic notification to a provider clinician(s) responsible for the care of the patient; generating and providing a recommendation for modifying a care plan or treatment procedure associated with the patient; or scheduling healthcare resources for the patient.

8. The media of claim 7, wherein the electronic notification includes information indicating the determined likelihood of the patient experiencing the acute inflammatory condition.

9. The media of claim 1, wherein the modified computer code executed in a healthcare software program comprises a software healthcare agent associated with a care plan or treatment procedure associated with the patient.

10. The media of claim 1, wherein the vital signs time series comprises at least forty serial measurements with corresponding date-time information.

11. The media of claim 1, wherein the acute inflammatory condition comprises systemic inflammatory response syndrome, sepsis, severe sepsis, or septic shock.

12. A system for forecasting an emergent acute inflammatory condition or event in a patient, comprising:
    one or more sensors configured to acquire physiological data from the patient;
    one or more processors;
    memory storing computer-useable instructions that, when executed by the one or more processors, implement a method comprising:
    acquiring, using the one or more sensors, vital signs values;
    determining a time series from the acquired vital signs values;
    generating a linear model and a cusp catastrophe-theoretic model based on the determined time series;
    quantitatively evaluating the linear model and the cusp catastrophe-theoretic model to determine which model describes a variation in the time series;
    determining a performance criterion time series by selecting the model that describes the variation in the time series;
    evaluating the performance criterion time series using a threshold;
    based on the evaluating, determining an elevated risk of an acute inflammatory event for the patient; and
    based on the determined elevated risk, automatically modifying computer code executed in a healthcare software program for treating the patient, thereby transforming the healthcare software program.

13. The system of claim 12, wherein in the vital signs comprise a heart rate (HR), a systolic blood pressure (SBP), and a respiratory rate (RR) of the patient.

14. The system of claim 13, further comprising deriving a multiplicative rate-pressure-product (RPP) from the HR and the SBP.

15. The system of claim 12, further comprising smoothing the performance criterion time series.

16. The system of claim 15, wherein the smoothing the performance criterion time series is performed by an Exponentially-Weighted Moving Average (EWMA) operation.

17. The system of claim 12, wherein the performance criterion time series comprises a goodness-of-fit metrics time series, and further comprising determining transgression(s) of a reference range for the goodness-of-fit metrics time series, thereby determining a near-term risk of an acute inflammatory event.

18. The system of claim 12, further comprising a data store configured for storing and logging indications associated with a forecasted acute inflammatory event for the patient, and configured for use in preventing or mitigating a severity of a subsequent acute inflammatory event.

19. The system of claim 12, wherein the cusp catastrophe-theoretic model is generated using subsets of measurements of the criterion time series, such that each subset comprises a plurality of approximately co-synchronous measurements at least forty time points.

20. The system of claim 12, wherein the inflammatory condition comprises systemic inflammatory response syndrome, sepsis, severe sepsis, or septic shock.

* * * * *